United States Patent [19]
Minachev et al.

[11] 4,036,782
[45] July 19, 1977

[54] GRANULATED ZEOLITE CATALYST AND PROCESS FOR PRODUCING THE CATALYST

[76] Inventors: Khabib Minachevich Minachev, Leninsky prospekt, 57, kv. 15; Evgeny Sergeevich Mortikov, Leninsky prospekt, 61/1, kv. 34, both of, Moscow; Alexandr Semenovich Leontiev, ulitsa Gagarina, 13, kv. 13, Bashkirskaya ASSR, Salavat; Tamara Stepanovna Papko, Leninsky prospekt, 67, kv. 54, Moscow; Alexei Alexeevich Masloboev-Shvedov, Nagatinskaya naberezhnaya, 16, kv. 75, Moscow; Nikolai Fedorovich Kononov, ulitsa Garibaldi, 13/54 korpus 2, kv. 41, Moscow, all of U.S.S.R.

[21] Appl. No.: 537,764
[22] Filed: Dec. 31, 1974
[51] Int. Cl.² .............................................. B01J 29/06
[52] U.S. Cl. .................................................. 252/455 Z
[58] Field of Search ................................... 252/455 Z

[56] References Cited

U.S. PATENT DOCUMENTS

| 3,140,249 | 7/1964 | Plank et al. | 252/455 Z |
| 3,262,890 | 7/1966 | Mitchell et al. | 252/455 Z |
| 3,402,996 | 9/1968 | Maher et al. | 252/455 Z |
| 3,494,854 | 2/1970 | Gallagher et al. | 252/455 Z |

*Primary Examiner*—Carl F. Dees
*Attorney, Agent, or Firm*—Fleit & Jacobson

[57] ABSTRACT

A granulated zeolite catalyst which contains cations of metals of Group II of the periodic system with an exchange degree of from 5 to 50% of the theoretical value, hydrogen groups with an exchange degree of from 5 to 50% of the theoretical value, and at least one of the two following components, the first representing cations of metals of Group III of the periodic system with an exchange degree of from 20 to 90% of the theoretical value, the second representing cations of transition metals of Group IV of the periodic system with an exchange degree of from 9 to 80% of the theoretical value.

12 Claims, No Drawings

GRANULATED ZEOLITE CATALYST AND PROCESS FOR PRODUCING THE CATALYST

A process for producing a granulated zeolite catalyst which comprises granulation of the starting zeolite. This granulation may be also performed in the presence of a binder in an amount ranging from 10 to 30% by weight of the starting zeolite as calculated on the dry product. The resulting granules are dried at 10°-150° C and calcined at 380°-550° C. The calcined granules are treated at 70°-90° C with aqueous solutions of salts of metals of Group II of the periodic system and/or with aqueous solutions of ammonium salts, dried at 120°-150° C and calcined at 380°-550° C. The granules resulting from the second calculation are treated at 40°-90° C with at least one of two components, the first comprising aqueous solutions of salts of metals of Group III of the periodic system, the second aqueous solutions of salts of transition metals of Group IV of the periodic system. Therewith, in the case of treating the granules resulting from the first calcination with aqueous solutions of ammonium salts, the granules resulting from the second calcination, in addition to the treatment thereof with at least one of the two above-mentioned components, are also treated with aqueous solutions of salts of metals of Group II of the periodic system. The granules resulting from these operations are dried at 120°-150° C and calcined at 380° to 550° C. In the process of the present invention the starting zeolite may be first treated with aqueous solutions of salts of metals of Group II of the periodic system and/or with aqueous solutions of ammonium salts at a temperature of 40° to 95° C. The resulting exchanged zeolite is dried at 100°-150° C and mixed with a binder as mentioned hereinbefore. The mixture is granulated and the granules are dried at 100°-120° C and calcined at 380° to 550° C. The calcined granules are treated with aqueous solutions of salts of metals of Group III and/or IV of the periodic system, and when required, with aqueous solutions of ammonium salts followed by drying and calcination similar to those described hereinbefore. The catalyst of the present invention features a high activity and stability.

The present invention relates to granulated zeolite catalysts and processes for producing catalysts.

These catalysts are extensively used for hydrocarbon conversion processes such as alkylation of aromatic and paraffin hydrocarbons with olefins and realkylation of alkylaromatic hydrocarbons. These processes serve as basic ones for the large-scale commercial production of ethylbenzene, cumene, butylbenzenes, high-octane alkylbenzines and the like.

Known in the art are processes for the production of such products using catalysts based on aluminium chloride. The use of such catalysts requires special process equipment for drying, preparation, separation, neutralization of the catalytic complex, disposal of acidic gases and industrial waste water. Moreover, the use of such catalysts necessitates special safety measures, corrosion protection of the equipment; it is also accompanied by substantial consumption rates of aluminium chloride, soda and water.

These disadvantages are eliminated by the use of granulated zeolite catalysts.

Thus, known in the art is a granulated zeolite catalyst for processes of alkylation and realkylation of hydrocarbons.

The catalyst contains metal cations in various combinations; it may also contain hydrogen groups. For example, the catalyst may contain cations of metals of II or III Groups of the periodic system; cations of metals of Groups II and VIII of the periodic system; cations of metals of Group III of the periodic system and hydrogen groups.

This prior art catalyst features a disadvantage residing in a poor stability of its action which does not exceed 100 hours. Repeated regenerations of the catalysts result in an irreversible loss of its activity, i.e. "ageing". Such insufficient stability of the catalyst action results, in turn, in a reduced annual output of the final product, increased consumption rate of the catalyst, a complicated process flow sheet, and an increased number of technological operations.

It is an object of the present invention to provide such a granulated and zeolite catalyst which has improved activity and stability.

It is another object of the present invention to provide a process for producing a granulated zeolite catalyst possessing the above-mentioned properties.

These and other objects of the present invention are accomplished by that a granulated zeolite catalyst that contains cations of metals of Group II of the periodic system with an exchange degree of 5 to 50% of the theoretical value, hydrogen groups with an exchange degree of 5 to 50% of the theoretical value, and at least one of two components: the first representing cations of metals of Group III of the periodic system with an exchange degree of from 20 to 90% of the theoretical value; the second representing cations of transition metals of Group IV of the periodic system with an exchange degree ranging from 9 to 80% of the theoretical value.

Granulated catalyst with a combination of cations of metals and hydrogen groups according to the present invention ensures an optimal progress of reactions of alkylation and realkylation of hydrocarbons. Cations of metals of Group II of the periodic system, in particular calcium, hinder migration of cations of metals of Group III, for example, cations of rare-earth elements, aluminium and cations of transition metals of Group IV which are active centers, into the regions of zeolite crystal lattice which are inaccessible for reagents. This makes it possible to avoid "ageing" of catalysts which occurs after oxidative regenerations of zeolites not containing, for example, calcium cation. Cations of metals of Group II not only prolong the catalyst "life time" but contribute to a reduced coke-formation and, consequently, to an increased service life of the catalyst between regenerations. Specific combination of metal cations and the pressure of hydrogen groups also ensures the acidity range necessary for reactions, i.e. a set of centers having various acidic nature and force. Such acidic (proton) centers are formed during the formation of hydrogen form of the a zeolite as well as during water absorption on cations of metals of Group III and IV of the periodic system.

The above-described chemical composition of the catalyst is obtained due to a specified sequence of technological operations of cation exchange, drying and calcination.

A process for producing a granulated zeolite catalyst in accordance with the present invention resides in that the starting zeolite is granulated, the resulting granules are dried at 100° to 150° C, calcined at a temperature within the range of from 380° to 550° C, whereafter the calcined granules are treated with aqueous solutions of salts of metals of Group II of the periodic system and/or with aqueous solutions of ammonium salts at a temperature ranging from 70° to 90° C, dried at a temperature within the range of from 120° to 150° C and calcined at a temperature of from 380° to 550° C; the granules resulting from the second calcination are treated at a temperature of from 40° to 90° C with at least one of two components: the first representing aqueous solutions of salts of metals of Group III of the periodic system, while the second component represents aqueous solutions of salts of transition metals of Group IV of the periodic system; in the case of treating the granules resulting from the first calcination with aqueous solutions of ammonium salts, the granules resulting from the second calcination, in addition to the treatment with at least one of said two components, are also treated with aqueous solutions of salts of metals of Group II of the periodic system; the granules obtained as a result of the thus-performed operations are dried at a temperature ranging from 120° to 150° C and calcined at 380° to 550° C.

The starting zeolite may be used in the form of a powder, suspension or in the form of ready-to-use granules. In this latter case the steps of granulation, drying and calcination of the resulting granules are avoided.

Zeolite treatment with salt solutions within said temperature range ensures substitution of cations in the starting zeolite for cations of corresponding metals as well as ammonium cation present in the solution. Drying and calcination are necessary to prevent granules from cracking during the catalyst operation at elevated temperatures. In particular, calcination is necessary to increase the depth of exchange of zeolite cations, while in the case of treating calcined granules with ammonium salts — for the transformation of ammonium form of the zeolite into its hydrogen form.

Exchange of cations of the starting zeolite for hydrogen groups is effected not only due to the treatment of calcined granules with ammonium salts with subsequent decomposition of the zeolite ammonium form but also by way of treating the granules resulting from the second calcination with aqueous solutions of the above-mentioned salts of metals of Group III and transition metals of Group IV with an increased acidity (pH = 1 to 3).

In the case of treating granules resulting from the first calcination with aqueous solutions of salts of metals of Group II of the periodic system, the treatment with aqueous solutions of ammonium salts may be performed both prior to the treatment of twice-calcined granules with aqueous solutions of metal salts of Group III and aqueous solutions of transition metals of Group IV of the periodic system, and simultaneously therewith. In the latter case, ammonium salts reduce the reaction medium acidity thus preventing zeolite crystal structure from breaking.

To improve processability of the starting zeolite and ensure the required mechanical strength of the catalyst and an optimal size of secondary pores, it is advisable that the starting zeolite be granulated in the presence of a binder in an amount of from 10 to 30% by weight of the starting zeolite calculation based on the dry product.

When the starting zeolite is used in the form of a suspension, the latter should be washed, prior to granulation of the starting zeolite, to a pH of 7-9 of the washings and then dried at a temperature within the range of from 110° to 150° C; the resulting mass should be mixed with a binder in the amounts mentioned hereinabove. Otherwise, the zeolite is difficult to granulate and the final catalyst shows but a low strength.

As the binder use may be made of aluminium hydroxide, aluminium hydroxynitrate, bentonite clay taken either separately or in various combinations.

Bentonite clay whenever used either separately or in combination with another binder partially fills secondary pores of the catalyst thus impairing its selectivity. In order to avoid this phenomenon, it is advisable that the granules resulting from the second calcination, prior to the treatment thereof with aqueous solutions of salts of metals of Group II of the periodic system and/or with aqueous solutions of ammonium salts, be treated with aqueous alkaline solutions at a temperature within the range of from 20° to 90° C. Due to this treatment, bentonite clay is partially removed by leaching.

Granulation of the starting zeolite in the presence of a binder in the above-mentioned amounts may be preceded by a treatment of the starting zeolite with aqueous solutions of salts of metals of Group II of the periodic system and/or aqueous solutions of ammonium salts and subsequent drying. This ensures a more intimate contact of the solution with the bulk of zeolite which, in turn, results in a greater exchange degree at a higher rate of the exchange reaction. Exchanged zeolite is easily granulated; this, however, is accompanied by great losses of the zeolite.

In this case, production of granulated zeolite catalyst of the above-mentioned composition is effected in the following manner: the starting zeolite is treated with aqueous solutions of salts of metals of Group II of the periodic system and/or aqueous solutions of ammonium salts at a temperature ranging from 40° to 95° C; dried at a temperature within the range of from 100° to 150° C, mixed with a binder which is taken in an amount of from 10 to 30% by weight of the starting zeolite calculated on dry product; the resulting mixture is granulated and the granules thus produced are dried at a temperature within the range of from 100° to 120° C and calcined at a temperature of from 380° to 550° C; the calcined granules are treated at 40°–90° C with at least one of the two following components, the first being in the form of aqueous solutions of salts of metals of Group III of the periodic system, the latter representing aqueous solutions of salts of transition metals of Group IV of the periodic system; therewith, in the case of treating the starting zeolite with aqueous solutions of ammonium salts the calcined granules, in addition to treating with at least one of the two above-mentioned components, are treated with aqueous solutions of salts of metals of Group II of the periodic system; the granules resulting from these operations are dried at 120°–150° C and calcined at a temperature of from 380° to 550° C.

In the case of treating the starting zeolite with aqueous solutions of salts of metals of Group II of the periodic system, the calcined granules, in addition to the treatment thereof with at least one of the two above-mentioned components may be also treated with aqueous solutions of ammonium salts.

As the binder use is made of aluminium hydroxide, aluminium hydroxynitrate, bentonite clay employed either separately or in various combinations.

The process of the present invention makes it possible to produce a granulated zeolite catalyst featuring a continuous action service for at least 3,000 hours. The use of the catalyst of the above-mentioned composition makes it possible to increase annual output of the final product, reduce coke-formation by 1.5-2 times, preclude ageing of the catalyst and, thereby, reduce its consumption rate. In addition, the catalyst produced in accordance with the process of the present invention features a wider operation range, whereby it may be employed in a less expensive adiabatic reactor.

Catalytic processes using the catalyst thus produced occur at lower temperatures. Thus, a process of benzene alkylation with ethylene is effected at a temperature within the range of from 150° to 200° C instead of 250°-300° C; alkylation with propylene and butene is effected at a temperature within the range of from 100° to 150° C instead of 200°-250° C.

All these advantages contribute to a considerable simplification of the process scheme, result in a lesser number of technological steps and better economical efficiency of processes.

The process for producing the catalyst of the present invention is rather simple and is embodied as follows.

As it has been already mentioned hereinbefore, the starting zeolite is employed in the form of a powder, suspension or granules. When a zeolite is employed in a powder-like form, it is dried, crushed, charged into a paddle mixer, and mixed for a period of 30 to 60 minutes. Thereafter, it is combined with a binder such as aluminium hydroxide, aluminium hydroxynitrate, bentonite clay employed either separately or in various combinations. The binder is taken in an amount of from 10 to 30% by weight of the starting zeolite calculated on the dry product. The mixture is thoroughly agitated. During the mixing stage water is added to the mixture until it amounts to 40-50% by weight of the mixture. As a result, a paste is obtained which is then discharged from the mixer, plastified and then granulated by conventional methods.

When a zeolite is to be granulated without using a binder, the starting zeolite is moulded into granules by conventional methods and the resulting granules are treated with an aqueous solution of an alkali or a salt thereof.

The granules are dried at a temperature within the range of from 100° to 150° C and subjected to calcination at a temperature ranging from 380° to 550° C.

When the starting zeolite is employed in the form of an aqueous suspension, the latter is washed with water to a pH = 7 to 9 of the washings, dried at a temperature within the range of from 110° to 150° C; the resulting mass is mixed with the binder mentioned hereinbefore, and then granulated. Further sequence of technological steps for treating the granules is the same.

When bentonite clay is used as the binder, the calcined granules are treated with an aqueous solution of an alkali at a temperature of from 20° to 90° C to partly remove (by leaching) bentonite clay and then washed with water.

Calcined granules are charged into a reactor provided with a jacket and treated, under stirring, with an aqueous solution of salts of metals of Group II of the periodic system and/or with an aqueous solution of an ammonium salt at a temperature within the range of from 70° to 90° C to substitute sodium ions in the zeolite. After this treatment, the zeolite granules are washed with water until anions are not detected in the washings, dried at a temperature ranging from 120° to 150° C and calcined at 380°-550° C. After calcination, the granules are again charged into the jacketed reactor and treated at a temperature of from 40° to 90° with aqueous solutions of salts of metals of Group III of the periodic system and/or with aqueous solutions of salts of transition metals of Group IV; therewith, during the treatment of the granules resulting from the first calcination with aqueous solutions of ammonium salts, in addition to the above-said treatment of the granules resulting from the second calcination, a treatment is effected by means of aqueous solutions of metal salts of Group II of the periodic system. During the treatment of the granules resulting from the first calcination by means of aqueous solutions of metal salts of Group II of the periodic system, there is no necessity to treat the granules resulting from the second calcination with aqueous solutions of ammonium salts. After said treatment the granules are again washed free from anions, dried at a temperature ranging from 120° to 150° C and calcined at a temperature of from 380° to 550° C.

When the starting zeolite is employed in the form of granules, the latter are charged into a reactor and treated with aqueous solutions of salts of metals of Group II and/or with aqueous solutions of ammonium salts. Further sequence of technological steps is the same.

The starting zeolite may be first treated with aqueous solutions of salts of metals of Group II of the periodic system and/or aqueous solutions of ammonium salts at a temperature of from 40° to 95° C. The resulting exchange zeolite is dried at a temperature within the range of from 100° to 150° C and mixed with a binder in accordance with the above-described procedure. The resulting mixture is granulated by conventional methods; the resulting granules are dried at a temperature of from 100 to 120° C and calcined at 380°-550° C. The calcined granules are charged into a reactor provided with a jacket and treated with aqueous solutions of salts of metals of Group III and/or IV of the periodic system and, when required, with aqueous solutions of ammonium salts, followed by drying and calcination performed in accordance with the procedures described herein above.

For better understanding of the present invention, some specific Examples are given hereinbelow.

Data on exchange degree values are given as calculated on the theoretical.

EXAMPLE 1

Powder-like zeolite NaY with the molar ratio $SiO_2:Al_2O_3 = 4.7$ in the amount of 500 kg is mixed with aluminum hydroxide taken in the amount of 30% by weight of the starting zeolite as calculated based on the dry product. The mixture is agitated, and combined with water to the content thereof in the mixture of 45 wt.%. The resulting paste is plastified and extruded into granules of a 4×4 mm size. The granules are air-dried for 12 hours, then for 6 hours at a temperature of from 10° to 120° C. Thereafter, the granules are calcined at a temperature ranging from 400° to 500° C for 10 hours.

The calcined granules are charged into an apparatus provided with a jacket and twice treated, under stirring, with a 10% aqueous solution of calcium chloride at a temperature of 85°-95° C. The solution is prepared on the basis of 3 equivalents of calcium per 1 equivalent of sodium in the starting zeolite. Ech treatment lasts for 2 hours. After each treatment the zeolite granules are dried for 6 hours at 120°-150° C and calcined at 550° C for 6 hours. The calcined granules are charged into a jacketed apparatus and twice treated with a mixture of 5% aqueous solutions of chlorides of rare-earth elements and ammonium nitrate at a temperature of 85°–90° C. The solutions are prepared on the basis of 3 equivalents of rare-earth elements and 2 equivalents of ammonium per one equivalent of sodium in the starting zeolite. Each treatment is effected for 1 hours. After each treatment the zeolite granules are washed with water until chloride and nitrate ions are not detected in the washings, dried for 3 hours at 120°–150° C and calcined for 5 hours at 400°–550° C.

The bulk weight of the resulting catalyst is 0.70 g/cm$^3$; mechanical strength at 20° C is 0.3 kg/mm$^2$; static capacity as measured with benzene at 20° C is 31%; acidity measured with butylamine is 0.78 mequiv./g.

Exchange degree for calcium is 9%; that with respect to rare-earth elements is 62%; and with respect to hydrogen group is 28%.

300 l of the resulting catalyst (280 kg) are placed into an adiabatic reactor. A mixture of benzene and ethylene at a molar ratio thereof ranging from 6:1 to 8:1 respectively is passed through the reactor at a space velocity of 2 to 4 hr$^{-1}$ at a temperature within the range of from 150° to 200° C under a pressure of 20–25 atm. Ethylene conversion rate for 300 hours of a continuous operation of the reactor without any regeneration is 80 to 100%.

Multiple oxidizing regenerations of the catalyst at a temperature within the range of from 450° to 700° C did not reduce its initial activity.

EXAMPLE 2

A powder-like zeolite NaY with the molar ratio SiO$_2$:Al$_2$O$_3$ = 5 in the amount of 12 kg is placed into an apparatus provided with a jacket and treated, under stirring, five times with a 5% aqueuos solution of calcium chloride at a temperature of 70°–80° C. Each treatment lasts for 6 hours. The solution is prepared on the basis of 5 equivalents of calcium per 1 equivalent of sodium in the starting zeolite. After each treatment the zeolite is washed with water until no chloride ions are detected in the washings and dried at a temperature within the range of from 120° to 150° C. Thereafter the zeolite is mixed with aluminum hydroxide taken in the amount of 30% by weight of the starting zeolite as calculated based on the dry product. The mixture is agitated and added combined with water to the content thereof in the mixture of 50 wt.%. The resulting paste is plastified and extruded into granules of a 5×6 mm size. The granules are air-dried for 20 hours, and then at 100°–120° C for 6 hours. Thereafter, the granules are calcined at 380° C for 6 hours and at 550° for 6 hours as well.

The calcined granules are charged into an apparatus with a jacket and treated thrice, under stirring, with a mixture of 7% aqueous solutions of chlorides of rare-earth elements and ammonium chloride at a temperature of from 60° to 70° C. The solution are prepared on the basis of 3 equivalents of rare-earth elements and 2 equivalents of ammonium per 1 equivalent of sodium in the starting zeolite. Duration of each treatment is 6 hours. After each treatment the zeolite granules are washed with water until no chloride ions are detected in the washings, dried for 3 hours at a temperature of from 120° to 150° C and calcined at 550° c for 6 hours.

The resulting catalyst bulk weight is 0.65 g/cm$^3$; its mechanical strength at 20° C is 0.8 kg/mm$^2$; static capacity with respect to benzene at 20° C is 38%; activity with respect to butylamine is 0.78 mequiv/g.

Exchange degree for calcium is 5%; for rare-earth elements is 80%; and for hydrogen group is 10%.

One liter of the resulting catalyst (0.65 kg) is charged into an adiabatic reactor. A mixture of benzene and ethylene at the molar ratio of 4:1 respectively is passed through the reactor at the space velocity of 3 hr$^{-1}$ at a temperature of 180°–220° C under 30 atm pressure. Ethylene conversion rate during 1,100 hours of continuous action of the catalyst without regeneration is 80 to 100%.

EXAMPLE 3

Granulation of a zeolite NaY with the molar ratio SiO$_2$; Al$_2$O$_3$ = 3.8 without a binder is effected by tabletting with subsequent treatment of the resulting granules with aqueous solutions of an alkali or salt thereof. The zeolite granules are dried at 100° to 150° C for 6 hours and calcined at 550° C for 6 hours.

The calcined granules in the amount of 1.5 kg are placed into an apparatus provided with a jacket and treated thrice, under stirring, with a 5% aqueous solution of calcium chloride at a temperature within the range of from 70° to 80° C. The solution is prepared on the basis of 5 equivalents of calcium per one equivalent of sodium in the starting zeolite. Duration of each treatment is 4 hours. After each treatment the granules are washed with water until no chloride ions are detected in the washings, dried for 6 hours at a temperature of from 120° to 150° C and calcined at the temperature of 550° C for 6 hours.

The calcined granules are again charged into a jacketed apparatus and treated twice, under stirring, with a mixture of 5% aqueous solutions of chlorides of rare-earth elements and ammonium chloride at a temperature of from 70° to 80° C. The solutions are prepared on the basis of 3 equivalents of rare-earth elements and 2 equivalents of ammonium per one equivalent of sodium in the starting zeolite. Duration of each treatment is 4 hours. After each treatment the zeolite granules are treated with water until no chloride ions are detected in the washings, dried for 3 hours at a temperature of from 120° to 150° C, and calcined for 6 hours at 550° C.

The resulting catalyst bulk weight is 0.62 g/cm$^3$, mechanical strength at 20° C is 0.8 kg/mm$^2$; static capacity with respect to benzene at 20° C is 37%, acidity with respect to butylamine is 0.68 mequiv./g.

Exchange degree for calcium is 15%; for rare-earth elements is 75%; and for hydrogen group is 9%.

One liter of the resulting catalyst (0.62 kg) is charged into an adiabatic reactor. A mixture of benzene and ethylene at the molar ratio of 4:1 respectively is passed through the reactor at the space velocity of 3 hr$^{-1}$ at a temperature of 200° to 220° C under the pressure of 30 atm. Ethylene conversion during 1,000 hours of continuous operation of the catalyst without regeneration is as high as 70 to 98%.

50 cm$^3$ of the resulting catalyst are placed into an isothermal reactor. A mixture of benzene and ethylene at the molar ratio of 3:1 respectively is passed through the reactor at the space velocity of 4 hr$^{-1}$ at a temperature within the range of from 150° to 350° C under 30 atm pressure. Ethylene conversion ranges from 60 to 100% depending on temperature. Selectivity with respect to ethylbenzene is about 90%. Amount of coke deposited on the catalyst for the first 6 hours of its operation varied from 1 to 4% by weight of the catalyst as compared to 10–16% by weight of catalyst based on NaY and containing rare-earth elements.

EXAMPLE 4

A powder-like zeolite with the molar ratio $SiO_2:Al_2O_3 = 4.6$ in the amount of 15 kg is mixed with aluminum hydroxide taken in the amount of 25% by weight of the starting zeolite as calculated based on the dry product. The mixture is agitated and combined with water to the content thereof in the mixture of 45 wt.%. The resulting paste is plastified and extruded into granules of a 4×4 mm size. The granules are air-dried for 16 hours, then at 100°–120° For 6 hours, and calcined for 12 hours at 500° C.

The calcined granules are charged into an apparatus provided with a jacket and twice treated, under stirring, with a 10% calcium chloride solution at a temperature within the range of from 80° to 90° C. The solution of calcium chloride is prepared on the basis of 3 equivalents of calcium per one equivalent of sodium in the starting zeolite. Duration of each treatment is 6 hours. After each treatment the zeolite granules are washed with water until no chloride ions are detected in the washings, dried for 6 hours at a temperature of from 120° to 150° C and calcined for 6 hours at 550° C.

The calcined granules are charged into an apparatus provided with a jacket and twice treated, under stirring, with a mixture of 10% aqueous solutions of chlorides of rare-earth elements and ammonium chloride at a temperature of 60°–70° C. The solutions are prepared on the basis of 3 equivalents of rare-earth elements and 2 equivalents of ammonium per one equivalent of sodium in the starting zeolite. Each treatment lasts for 4 hours. After each treatment the zeolite granules are washed with water until no chloride ions are detected in the washings, dried for 6 hours at 120°–150° C and calcined for 6 hours at 550° C.

The resulting catalyst bulk weight is 0.70 g/cm$^3$; mechanical strength at 20° C is 0.2 kg/mm$^2$; static capacity with respect to benzene at 20° C is 32%; acidity with respect to butylamine is 0.79 mequiv./g.

Exchange degree for calcium is 18%; for rare-earth elements is 60%; and for hydrogen group is 20%.

One liter of the resulting catalyst (0.70 kg) are charged into an adiabatic reactor. A mixture of benzene and ethylene at a molar ratio of 4:1 to 6:1 respectively is passed through the reactor at the space velocity of 3 hr$^{-1}$ at a temperature within the range of from 170° to 250° C under 30 atm pressure. Conversion of ethylene for 3,000 hours of continuous operation of the catalyst with two oxidizing regenerations is 80–100%.

EXAMPLE 5

A powder-like zeolite NaY with the molar ratio $SiO_2:Al_2O_3 = 4.7$ in the amount of 300 g is mixed with aluminum hydroxy nitrate taken in the amount of 16% by weight of the starting zeolite as calculated based on the dry product. The mixture is agitated and combined with water to the content thereof in the mixture of 50% by weight. The paste thus prepared is plastified and then formed into granules by a pasting-in method to obtain granules of a 4×4 mm size. The granules are air-dried for 12 hours, then at a temperature within the range of from 100° to 120° C for 6 hours, and calcined for 6 hours at 550° C.

The calcined granules of the zeolite NaY are placed into a flask and twice treated, under stirring, with a 10% aqueous solution of calcium chloride at a temperature of from 70° to 90° C. The solution is prepared on the basis of 2 equivalents of calcium per one equivalent of sodium in the starting zeolite. Duration of each treatment is 2 hours. After each treatment the zeolite granules are the with water until no chloride ions are detected in washings, dried for 6 hours at 120°–150° C and calcined for 6 hours at 500° C.

The calcined granules of the zeolite CaY are placed into a flask and treated, under stirring, with a 10% aqueous solution of nitrates of rare-earth elements with the pH = 1.5 at a temperature within the range of from 40° to 60° C. The solution is prepared on the basis of 0.75 equivalent of rare-earth elements per 1 equivalent of sodium in the starting zeolite. Duration of the treatment is 2 hours. After this treatment the zeolite granules are washed with water till no nitrate ions are detected in the washings. Thereafter, the granules are dried for 6 hours at a temperature ranging from 120° to 150° C and calcined at 400°–500° C for 6 hours.

The resulting catalyst bulk weight is 0.70 g/cm$^3$; its mechanical strength at 20° C is 0.3 kg/mm$^2$; static capacity with respect to benzene at 20° C is 31%; acidity with respect to butylamine is 0.81 mequiv./g.

Exchange degree for calcium is 50%, for rare-earth elements is 42%, and for hydrogen group is 5%.

50 cm$^3$ (35 g) of the resulting catalyst are placed into an isothermal reactor. A mixture of isobutane with a mixture of n-butenes at the molar ratio of 10:1 respectively is passed through the reactor at the space velocity of 3 hr$^{-1}$ at the temperature of 80° C under 20 atm pressure. Conversion to alkylbenzines is about 100%.

EXAMPLE 6

Calcined granules of a zeolite NaY prepared in a manner similar to that described in Example 5 are changed, in the amount of 100 g, into a flask and twice treated, under stirring, with a 10% aqueous solution of magnesium nitrate at a temperature within the range of from 70 to 90° C. The solution is prepared on the basis of 2 equivalents of magnesium per one equivalent of sodium in the starting zeolite. Each treatment lasts for 2 hours. After each treatment the zeolite granules are washed with water until no nitrate ions are detected in the washings, dried for 6 hours at a temperature of from 120° to 150° C and calcined for 6 hours at 550° C.

The calcined granules are charged into a flask and treated under stirring with a 7% aqueous solution of nitrates of rare-earth elements with the pH = 2 at a temperature of 40° to 60° C. The solution is prepared on the basis of 0.75 equivalent of rare-earth elements per one equivalent of sodium in the starting zeolite. Duration of the treatment is 2 hours. After this treatment the zeolite granules are washed with water till no nitrate ions are detected in the washings. Thereafter, the granules are dried for 6 hours at a temperature within the range of from 120° to 150° C and calcined for 6 hours at a temperature ranging from 400° to 500° C.

The resulting catalyst bulk weight is 0.70 g/cm$^3$; mechanical strength at 20°C is 0.3 kg/mm$^2$; static capactiy for benzene at 20° C is 38%; acidity with respect to butylamine 0.87 mequiv./g.

Exchange degree for magnesium is 26%; for rare-earth elements is 52%, and for hydrogen group is 18%.

50 cm$^3$ of the resulting catalyst (33 g) are charged into an isothermal reactor. A mixture of benzene and propylene in the molar ratio of 3:1 respectively is passed through the reactor at the space velocity of 3 hr$^{-1}$ at 150° C under 30 atm pressure. Conversion of ethylene is 90 to 95%.

EXAMPLE 7

Calcined granules of a zeolite CaY prepared in a manner similar to that described in Example 5 in the amount of 70 g are charged into a flask and treated under stirring with a 10% aqueous solution of nickel nitrate at a temperature of from 70° to 80° C. The solution is prepared on the basis of one equivalent of nickel per one equivalent of calcium in the starting zeolite. Duration of the treatment is 2 hours. After this treatment the zeolite granules are washed with water until no nitrate ions are detected in the washings, dried for 6 hours at 120° to 150° C and calcined for 6 hours at 400°-500° C.

The resulting catalyst bulk weight is 0.70 g/cm$^3$; mechanical strength at 20° C is 0.3 kg/mm$^2$, static capacity with respect to benzene at 20° C is 38%, acidity with respect to butylamine is 0.92 mequiv./g.

Exchange degree for calcium is 25%, for nickel is 70%, and for hydrogen group — 5%.

50 cm$^3$ of the resulting catalyst (35 g) are charged into an isothermal reactor. A mixture of benzene and ethylene at the molar ratio of 3:1 respectively is passed through the reactor at the space velocity of 3 hr$^{-1}$ at 150° C under 30 atm pressure. Conversion of ethylene to secondary butylbenzene is 60%.

EXAMPLE 8

A powder-like zeolite NaY with the molar ratio SiO$_2$:Al$_2$O$_3$= 4.5 in the amount of 150 g is mixed with aluminium hydroxide taken in the amount of 20% by weight of the starting zeolite as calculated on the dry product. The mixture is agitated and combined with water to the content thereof in the mixture of 45% by weight. The resulting paste is plastified and then extruded into granules of a 4×4 mm size. The granules are predried for 12 hours in the air and then for 6 hours at a temperature of from 100° to 120°C and calcined for 6 hours at 550° C.

The calcined granules are charged into a flask and twice treated under stirring with a 10% solution of ammonium chloride at 80° C. The solution is prepared on the basis of 3 equivalents of ammonium per one equivalent of sodium in the starting zeolite. Each treatment lasts for 4 hours. After each treatment the zeolite granules are washed with water until no chloride ions are detected in the washings, dried for 6 hours at 120°-150° C and calcined at 550° C for 6 hours.

The calcined granules are charged into a flask and treated under stirring with a mixture of 10% aqueous solutions of nitrates of rare-earth elements, cadmium and cobalt at a temperature of from 60° to 70° C. The solution of nitrates is prepared on the basis of 0.5 equivalent of rare-earth elements, 0.5 equivalent of cadmium, 0.25 equivalent of cobalt per one equivalent of sodium in the starting zeolite. Duration of the treatment is 4 hours. After each treatment zeolite granules are washed with water until no nitrate ions are detected in the washings, dried for 6 hours at a temperature ranging from 120° to 150° C and calcined for 6 hours at a temperature of from 400° to 500° C.

The resulting catalyst bulk weight is 0.75 g/cm$^3$; mechanical strength at 20° C is 0.25 kg/mm$^2$, static capacity with respect to benzene at 20° C is 32%, acidity with respect to butylamine is 0.68 mequiv./g.

Exchange degree for cadmium is 19%, for rare-earth elements is 20%, for cobalt is 9%, and for hydrogen group is 30%.

50 cm$^3$ of the resulting catalyst (38 g) are charged into an isothermal reactor. A mixture of benzene and ethylene in the molar ratio of 3:1 respectively is passed through the reactor at the space velosity of 3 hr$^{-1}$ at the temperature of 200° C under 30 atm pressure. Ethylene conversion is 95-98%.

EXAMPLE 9

Calcined granules of a zeolite CaY prepared in a manner similar to that described in Example 5 in an amount of 70 g are charged into a flask and treated under stirring with a 7% aqueous solution of aluminium nitrate at a temperature ranging from 60° to 70° C. The solution is prepared on the basis of one equivalent of aluminium per one equivalent of calcium in the starting zeolite. The treatment duration is 2 hours. After this treatment the zeolite granules are washed with water until no nitrate ions are detected in the washings, dried for 6 hours at 120° to 150° C and calcined for 6 hours at 400 to 500° C.

The resulting catalyst bulk weight is 0.70 g/cm$^3$, mechanical strength with respect to benzene at 20° C is 28%, acidity with respect to butylamine is 0.65 mequiv./g.

Exchange degree for calcium is 28%, for aluminium is 54%, and for hydrogen group — 9%.

50 cm$^3$ of the resulting catalyst (35 g) are charged into an isothermal reactor. A mixture of benzene and ethylene in the molar ratio of 3:1 respectively is passed through the reactor at the space velocity of 3 hr$^{-1}$ at the temperature of 200° C under 30 atm pressure. Ethylene conversion is 85-90%.

EXAMPLE 10

A zeolite NaY in the form of a suspension with the molar ratio SiO$_2$:Al$_2$O$_3$ = 5.5 is washed on a filter-press with water to a pH of the washings of 8.5. The washed zeolite in the amount of 30 kg calculated based on the dry product is dried for 4–6 hours at a temperature within the range of from 110° to 150° C and mixed in a mixer with aluminium hydroxide and bentonite clay, each of the latter two components being taken in the amount of 10% by weight of the starting zeolite as calculated based on the dry product. The mixture is agitated, combined with water to the content thereof in the mixture of 40% by weight. The resulting paste is plastified and extruded into granules of a 4×4 mm size. The granules are dried for 6 hours at a temperature of from 100° to 120° C and calcined for 6 hours at a temperature within the range of from 380° to 550° C.

The calcined granules are charged into an apparatus provided with a jacket and twice treated, under stirring, with a 5% aqueous solution of an alkali such as NaOH at a temperature of from 60° to 80° C to remove the clay. Duration of the treatment is 4 hours. After this treatment the zeolite granules are washed with water to the pH=8 of the washings, whereafter they are twice treated with a mixture of 5% aqueous solutions of calcium and ammonium chlorides at a temperature of from 80° to 90° C. The solutions are prepared on the basis of 3 equivalents of calcium and one equivalent of ammonium per one equivalent of sodium in the starting zeolite. Each treatment lasts for 4 hours. After each treatment the zeolite granules are washed with water until no chloride ions are detected in the washings, dried for 3 hours at 120°-150° C and calcined for 6 hours at 380°-550° C.

The calcined granules are again charged into an apparatus provided with a jacket and twice treated under stirring with a 5% aqueous solution of nitrates of rare-earth elements at a temperature of from 80° to 90° C. The nitrate solution is prepared on the basis of 1.5 equivalents of rare-earth elements per one equivalent of sodium in the starting zeolite. Each treatment lasts for 4 hours. After each treatment the zeolite granules are washed with water until no nitrate ions are detected in the washings, dried for 3 hours at 120°-150° C and calcined for 6 hours at 380° C.

The resulting catalyst bulk weight is 0.75 g/cm$^3$; mechanical strength at 20° C is 0.8 kg/mm$^2$; static capacity with respect to benzene is 28% at 20° C; acidity with respect to butylamine is 0.68 mequiv./g.

Exchange degree for calcium is 14%, for rare-earth elements is 72%, and for hydrogen group is 13%.

One liter of the resulting catalyst (0.75 kg) is charged into an adiabatic reactor. A mixture of benzene and ethylene in a molar ratio of 4 - 6:1 respectively is passed through the reactor at a space velocity of 2 to 4 hr$^{-1}$ at a temperature within the range of from 170° to 250° C under 30 atm pressure. Conversion of ethylene is 80 to 100% during 1,100 hours of continuous operation of the catalyst without regeneration.

EXAMPLE 11

The catalyst of this Example is prepared in a manner similar to that of Example 2, except that the granules after granulation, drying and calcination are treated with a mixture of 2% aqueous solutions of chlorides of rare-earth elements and manganese chloride at the temperature of 40°C. The solution is prepared on the basis of 0.75 equivalent of rare-earth elements and 0.75 equivalent of manganese per one equivalent of sodium in the starting zeolite.(pH of the solution is 3):

The resulting catalyst bulk weight is 0.70 g/cm$^3$; mechanical strength at 20° C is 0.3 kg/mm$^2$; static capacity with respect to benzene at 20° C is 28%; acidity with respect to butylamine is 0.80 mequiv./g.

Exchange degree for calcium is 9%, for rare-earth elements is 47%, for manganese is 15%, and for hydrogen group is 24%.

EXAMPLE 12

The catalyst of this Example is prepared in a manner similar to that of Example 2, except that the starting powderlike zeolite NaY is twice treated with a 10% aqueous solution of ammonia at a temperature within the range of from 40° to 60°C. The solution is prepared on the basis of 3 equivalents of ammonia per one equivalent of sodium in the starting zeolite. The resulting granules after granulation, drying and calcination are treated with a mixture of 3% aqueous solutions of calcium chloride, zinc chloride and chlorides of rare-earth elements. The solution is prepared on the basis of 0.3 equivalent of calcium, 0.3 equivalent of zinc, and 0.3 equivalent of rare-earth elements per one equivalent of sodium in the starting zeolite.

The resulting catalyst bulk weight is 0.70 g/cm$^3$, mechanical strength at 20° C is 0.3 kg/mm$^2$; static capacity with respect to benzene at 20° C is 30%; acidity with respect to butylamine is 0.76 mequiv./g.

Exchange degree for calcium is 18%, for rare-earth elements is 41%, for zinc is 20%, and for hydrogen group is 18%.

EXAMPLE 13

A powder-like zeolite NaY with the molar ratio SiO$_2$:Al$_2$O$_3$ = 4.6 in the amount of 1.5 kg is mixed with bentonite clay taken in the amount of 30% by weight of the starting zeolite as calculated based on the dry product. The mixture is blended, combined with water to the content thereof in the mixture of 45 wt.%. The resulting paste is plastified and extruded into granules of a 4×4 mm size. The granules are pre-dried in the air for 12 hours and then dried for 6 hours at a temperature within the range of from 100° to 120° C. Thereafter, the granules are calcined at a temperature ranging from 400° to 500° C for 10 hours.

The calcined granules are charged into an apparatus with a jacket and twice treated, under stirring, with a 5% aqueous solution of NaOH at 20°-40° C to partially remove the clay. After this treatment which lasts for 4 hours, the zeolite granules are washed with water till pH=8 of the washings and then twice treated with a 10% aqueous solution of ammonium chloride at a temperature of from 80° to 90° C. The solution is prepared on the basis of 3 equivalents of ammonium per one equivalent of sodium in the starting zeolite. Duration of each treatment is 3 hours.

After each treatment the zeolite granules are washed with water until no chloride ions are detected in the washings, dried for 3 hours at a temperature within the range of from 120° to 150° C and calcined for 6 hours at a temperature within the range of from 380° to 550° C.

The calcined granules are again charged into an apparatus provided with a jacket and twice treated, under stirring, with a mixture of 5% aqueous solutions of nitrates of rare-earth elements and calcium nitrate at a temperature of 40°-60° C. The solution is prepared on the basis of 0.3 equivalent of calcium and 0.3 equivalent of rare-earth elements per one equivalent of sodium in the starting zeolite. Duration of each treatment is 6 hours. After each treatment the zeolite granules are washed with water until no nitrate ions are detected in the washings, dried for 3 hours at 120°-150° C and calcined for 6 hours at 550° C.

The resulting catalyst bulk weight is 0.70 g/cm$^3$; mechanical strength at 20° C is 0.4 kg/mm$^2$; static capacity with respect to benzene at 20° C is 28%; acidity with respect to butylamine is 0.85 mequiv./g.

Exchange degree for calcium is 22%, for rare-earth elements is 19%, and for hydrogen group is 51%.

50 cm$^3$ of the resulting catalyst (0.35 kg) are charged into an isothermal reactor. A mixture of benzene and ethylene in the molar ratio of 3:1 respectively is passed through the reactor at the space velocity of 3 hr$^{-1}$ at the temperature of 200° C under 30 atm pressure. Ethylene conversion is 70 to 90%.

EXAMPLE 14

The catalyst of this Example is prepared in a manner similar to that described in Example 10, except that instead of the mixture of aluminium hydroxide and bentonite clay use is made, as the binder, of aluminium hydroxynitrate in the amount of 20% of the zeolite weight calculated based on the dry product. In doing so, the stage of treating with an alkali is avoided.

The resulting catalyst bulk weight is 0.75 g/cm$^3$; mechanical strength at 20° C is 0.6 kg/mm$^2$; static capacity with respect to benzene at 20° C is 25%; acidity with respect to butylamine is 0.65 mequiv./g.

Exchange degree for calcium is 14%, for rare-earth elements is 60%, and for hydrogen group is 18%.

What is claimed is:

1. A granulated zeolite catalyst containing cations of metals of Group II of the periodic system with an exchange degree of from 5 to 50% of the theoretical value, hydrogen groups with an exchange degree of from 5 to 50% of the theoretical value and at least one component selected from the group consisting of cations of metals of Group III of the periodic system with an exchange degree of from 20 to 90% of the theoretical value and cations of transition metals of Group IV of the periodic system with an exchange degree of from 9 to 80% of the theoretical value.

2. A process for producing a granulated zeolite catalyst comprising forming the starting zeolite into granules, drying the resulting granules at a temperature ranging from 100° to 150° C and calcining the dried granules at 380°–550° C; treating the calcined granules at a temperature of from 70° to 90° C with at least one material selected from the group consisting of aqueous solutions of salts of metals of Group II of the periodic system and aqueous solutions of ammonium salts; drying the treated granules at a temperature of from 120° to 150° C and calcining the dried granules at a temperature of from 380° to 550° C; treating the granules resulting from the second calcination with at least one component selected from the group consisting of aqueous solutions of salts of metals of Group III of the periodic system and aqueos solutions of salts of transition metals of Group IV of the periodic system at a temperature of from 40° to 90° C; in the case of treating the granules resulting from the first calcination with aqueous solutions of ammonium salts, the granules resulting from the second calcination, in addition to being treated with said at least one component, are also treated with aqueous solutions of salts of metals of Group II of the periodic system; and drying the granules resulting from said operations at a temperature of from 120° to 150° C and calcining the dried granules at a temperature of from 380° to 550° C.

3. A process as claimed in claim 2, wherein in the case of treating the granules resulting from the first calcination with aqueous solutions of salts of metals of Group II of the periodic system, the granules resulting from the second calcination, in addition to the treatment with said at least one components, are treated with aqueous solutions of ammonium salts.

4. A process as claimed in claim 2, wherein the granulation of the starting zeolite is performed in the presence of a binder in an amount ranging from 10 to 30% by weight of the starting zeolite as calculated based on the dry product.

5. A process as claimed in claim 4, wherein as the binder is selected from the group consisting of aluminium hydroxide, aluminium hydroxynitrate and bentonite clay.

6. A process as claimed in claim 4, wherein the binder is bentonite clay and the granules resulting from the first calcination, prior to the treatment thereof with said at least one material are treated with aqueous alkali solutions at a temperature of from 20° to 90° C.

7. A process as claimed in claim 2, wherein the starting zeolite is used in the form of a suspension and, prior to the granulation of the starting zeolite, said suspension is washed with water to a pH of 7–9 of the washings, dried at a temperature of from 110° to 150° C, and the resulting mass is mixed with a binder in an amount of from 10 to 30% by weight of the starting zeolite as calculated based on the dry product.

8. A process as claimed in claim 7, wherein the binder is selected from the group consisting of aluminium hydroxide, aluminium hydroxynitrate and bentonite clay.

9. A process as claimed in claim 7, wherein the binder is bentonite clay and the granules resulting from the first calcination, prior to the treatment thereof with said at least one material, are treated with aqueous alkali solutions at a temperature of from 20° to 90° C.

10. A process for producing a granulated zeolite catalyst comprising treating the starting zeolite at a temperature of from 40° to 95° C with at least one material selected from aqueous solutions of salts of metals of Group II of the periodic system and aqueous solutions of ammonium salts; drying the treated zeolite at a temperature ranging from 100° to 150° C; mixing the dried zeolite with a binder in an amount ranging from 10 to 30% by weight of the starting zeolite as calculated based on the dry product; granulating the resulting mixture; drying the granules at a temperature of from 100° to 120° C and calcining the dried granules at a temperature of from 380° to 550° C; treating the calcined granules at a temperature of 40° to 90° C with at least one component selected from the group consisting of aqueous solutions of salts of metals of Group III of the periodic system and aqueous solutions of salts of transitions metals of Group IV; in the case of treating the starting zeolite with aqueous solutions of ammonium salts, the calcined granules in addition to being treated with said at least one components, are also treated with aqueous solutions of salts of metals of Group II of the periodic system; and drying the granules resulting from said operations at a temperature ranging from 120° to 150° C and calcining the dried granules at a temperature ranging from 380° to 550° C.

11. A process as claimed in claim 10, wherein in the case of treating the starting zeolite with aqueous solutions of salts of metals of Group II of the periodic system, the calcined granules, in addition to the treatment with said at least one components, are treated with aqueous solutions of ammonium salts.

12. A process as claimed in claim 10, wherein the binder a substance selected from the group consisting of aluminium hydroxide, aluminium hydroxynitrate and bentonite clay.

* * * * *